United States Patent
Al-Zeqri et al.

(10) Patent No.: US 10,494,722 B1
(45) Date of Patent: Dec. 3, 2019

(54) SULFONAMIDE CORROSION INHIBITORS

(71) Applicant: KING SAUD UNIVERSITY, Riyadh (SA)

(72) Inventors: Nabil Ahmed Qassim Al-Zeqri, Riyadh (SA); Isra Abd Alrhman Aboasbah, Nablus (PS); Ali Mohammed Alsalme, Riyadh (SA); Mohammed Suleiman Shtaya, Nablus (PS); Iyad Atallah Saadeddin, Nablus (PS); Abdelkader Zarrouk, Oujda (MA); Ismail Khalil Warad, Nablus (PS)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/391,138

(22) Filed: Apr. 22, 2019

(51) Int. Cl.
*C23F 11/16* (2006.01)
*C07C 303/38* (2006.01)
*C07C 311/05* (2006.01)

(52) U.S. Cl.
CPC .......... *C23F 11/164* (2013.01); *C07C 303/38* (2013.01); *C07C 311/05* (2013.01)

(58) Field of Classification Search
CPC ..... C23F 11/164; C07C 303/38; C07C 311/05
(Continued)

(56) References Cited

U.S. PATENT DOCUMENTS 4,060,522 A * 11/1977 Kindscher ............ C07D 295/26
  252/391
4,126,634 A * 11/1978 Thil ..................... C23F 11/164
  252/391

(Continued)

OTHER PUBLICATIONS

CID=103942579, National Center for Biotechnology Information (NCBI), PubChem Compound Database, Modify Date: Feb. 23, 2019, Create Date Jan. 13, 2016.

(Continued)

*Primary Examiner* — Ellen M McAvoy
(74) *Attorney, Agent, or Firm* — Richard C. Litman; Nath, Goldberg & Meyer (57) ABSTRACT

The sulfonamide corrosion inhibitors are compounds of formula A or formula B, as follows:

(Continued)

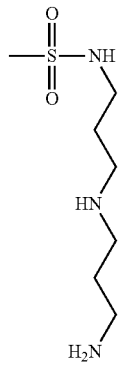

A

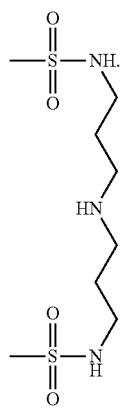

B

A method of synthesizing the sulfonamide corrosion inhibitors includes functionalizing a polyamine precursor with a sulfonyl chloride derivative by dehydrochlorination. The polyamine precursor may be bis(3-aminopropyl)amine and the sulfonyl chloride derivative may be methanesulfonyl chloride. The sulfonamide corrosion inhibitors may be applied alone or in any combination as corrosion inhibitors of a metal and are shown to be effective inhibitors of corrosion of iron or iron alloys in acidic conditions.

12 Claims, 9 Drawing Sheets

(58) Field of Classification Search
USPC .......................................... 252/391, 394, 395
See application file for complete search history.

(56) References Cited

U.S. PATENT DOCUMENTS

| | | | |
|---|---|---|---|
| 4,431,595 A * | 2/1984 | Hashimoto | B01F 17/0057 252/180 |
| 4,630,176 A | 12/1986 | Cuellar et al. | |
| 5,563,198 A | 10/1996 | Schilling | |
| 7,208,528 B1 | 4/2007 | Vermeulin et al. | |
| 7,291,217 B2 | 11/2007 | Phelps et al. | |
| 7,943,567 B2 | 5/2011 | Boggs et al. | |
| 9,611,560 B2 | 4/2017 | Lu et al. | |
| 2006/0180794 A1 * | 8/2006 | Goddard | C23F 11/173 252/387 |
| 2017/0226278 A1 | 8/2017 | Kasemi et al. | |

OTHER PUBLICATIONS

Kumari et al., "Electrochemical measurements for the corrosion inhibition of mild steel in 1M hydrochloric acid by using an aromatic hydrazide derivative", Arabian Journal of Chemistry (2017), vol. 10, Iss. 5, pp. 653-663.

Samide et al., "Corrosion Inhibition of Carbon Steel in Hydrochloric Acid Solution Using a Sulfa Drug", Chem. Biochem. Eng. Q. (2011), vol. 25(3), pp. 299-308.

* cited by examiner

SULFONAMIDE CORROSION INHIBITORS

BACKGROUND OF THE INVENTION

1. Field of the Invention

The present disclosure relates generally to corrosion inhibitors, and more particularly to two sulfonamide corrosion inhibitors derived from bis(3-aminopropyl)amine, namely, N-(3-((3-aminopropyl)amino)propyl)methanesulfonamide and N,N'-(azanediylbis(propane-3,1-diyl))dimethanesulfonamide, and the use thereof as corrosion inhibitors to inhibit corrosion of iron, mild steel, and similar metals.

2. Description of the Related Art

Metal corrosion, particularly by exposure to acidic conditions, causes significant economic, productivity and safety issues. Existing techniques to preserve a metal surface from corrosion are largely based on either controlling a potential of the metal surface, referred to as cathodic or anodic protection, or changing the nature of the metal surface by a physical or chemical coating.

Figure 1:
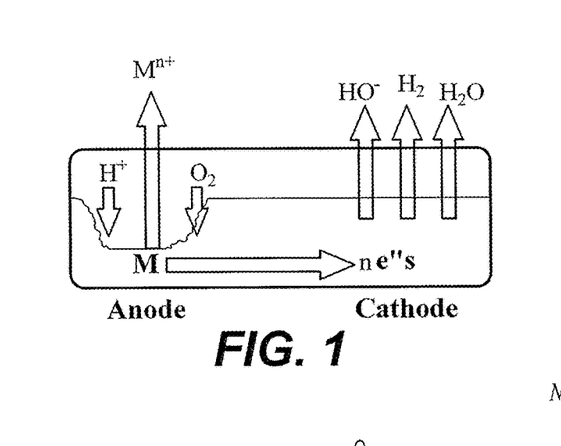
FIG. 1 is a schematic diagram depicting electrochemical corrosion of metal by an acid in the presence of oxygen.

A corrosion inhibitor is any chemical substance added to a solution or the metal surface that reduces the metal corrosion rate. Corrosion inhibitors can be classified by the mechanism of action, e.g., anodic, cathodic, both anodic and cathodic, or adsorption action (see FIG. 1), or by their chemical nature, e.g., inorganic or organic.

Organic corrosion inhibitors (OCIs) may be designed to have a wide array of structures and functionalities. OCIs may feature, for example, polar functional groups allowing for adsorption to the surface to be protected and providing protection by anodic, cathodic or both anodic and cathodic action, and further may protect the surface by forming a hydrophobic film that prevents the dissolution of the metal in the electrolyte. OCIs can adsorb onto a solution/metal interface via four primary mechanisms: (a) electrostatic attraction between the charged metal surface and the inhibitor; (b) interaction between the metal surface and P, N, O, S or n-electrons; (c) interaction between uncharged electron pairs of the inhibitor and the metal surface and (d) a combination of mechanisms (a) and (b).

Thus, sulfonamide corrosion inhibitors solving the aforementioned problems are desired.

SUMMARY OF THE INVENTION

The sulfonamide corrosion inhibitors are compounds of formula A or formula B, as follows:

A method of synthesizing the sulfonamide corrosion inhibitors may be performed under mild conditions by functionalizing a polyamine precursor with a sulfonyl chloride derivative by a dehydrochlorination reaction. In particular, the polyamine precursor may be norspermidine, i.e., N-(3-aminopropyl)-1,3-propanediamine, also known as bis (3-aminopropyl)amine and 3,3'-diaminodipropylamine, and the sulfonyl chloride derivative may be methanesulfonyl chloride. The polyamine precursor may be mixed with one or more solvents and the sulfonyl chloride derivative, in the absence or presence of basic conditions. The resulting sulfonamide corrosion inhibitors may be mono-substituted N-[3-(3-aminopropylamino)propyl]methanesulfonamide (compound A) or di-substituted N,N'-(azanediylbis(propane-3,1-diyl))dimethanesulfonamide (compound B).

The OCIs of the present subject matter may be applied alone or in any combination as corrosion inhibitors of a metal. In particular, the metal may be iron, mild steel, or another iron alloy in acidic conditions.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The sulfonamide corrosion inhibitors are compounds of formula A or formula B, as follows:

The method of synthesizing the sulfonamide corrosion inhibitors comprises functionalizing a polyamine precursor with a sulfonyl chloride derivative by dehydrochlorination. Specifically, the polyamine precursor may be norspermidine, i.e., N-(3-aminopropyl)-1,3-propanediamine, also known as bis(3-aminopropyl)amine and 3,3'-diaminodipropylamine, and the sulfonyl chloride derivative may be methanesulfonyl chloride. The resulting sulfonamide corrosion inhibitors may be mono-substituted N-[3-(3-aminopropyl)amino)propyl]methanesulfonamide (compound A) or di-substituted N,N'-(azanediylbis(propane-3,1-diyl)dimethanesulfonamide (compound B).

The sulfonamide corrosion inhibitors may be applied alone or in any combination as corrosion inhibitors of a metal. In particular, the metal may be iron, mild steel, or another iron alloy in acidic conditions, i.e., acidic aqueous solution, such as an aqueous HCl solution.

The following examples will further illustrate the sulfonamide corrosion inhibitors, the method of synthesizing the sulfonamide corrosion inhibitors, and the use of the synthesized sulfonamide compounds as corrosion inhibitors.

Example 1

Synthesis of Compound A and Compound B

Figure 2:
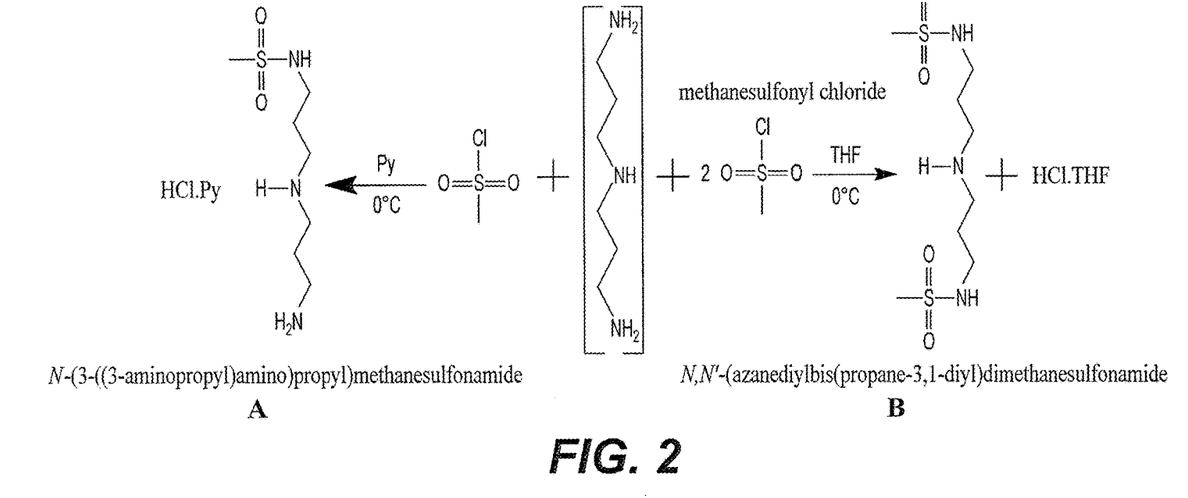
FIG. 2 is a reaction scheme for the synthesis of the sulfonamide corrosion inhibitors, viz., compounds A and B.

Exemplary sulfonamide corrosion inhibitors, starting from $N^1$-(3-aminopropyl)propane-1,3-diamine (otherwise referred to as 3,3 diaminodipropylamine), were synthesized as shown in FIG. 2.

To prepare compound A, one equivalent of methanesulfonyl chloride (0.50 g, 4.38 mmol) was dissolved in 40 mL of anhydrous tetrahydrofuran (THF) and 2 mL of anhydrous pyridine, to form a solution. The temperature of the solution was cooled down to 0° C. and was kept constant while 1 equivalent of 3,3 diaminodipropylamine dissolved in 10 mL of anhydrous THF was added drop by drop. After addition of the 3,3 diaminodipropylamine was completed, the solution was stirred for 2 hours or until the reaction was sufficiently complete. The reaction completeness was monitored by thin layer chromatography (TLC). The solid salt byproduct, including primarily pyridinium chloride, was removed by simple filtration, but may be removed in any conventional way known to one skilled in the art. The resulting filtrate, containing the desired product, was left overnight, allowing for evaporation of the THF solvent. After THF evaporation, the solid product comprising compound A was washed with n-hexane, then acetone, and then with dichloromethane, to produce a final amount of compound A. The above method produced 0.85 g of compound A, or a 92% yield. To prepare compound B, the same method as above was used, but two equivalents of methanesulfonyl chloride was used and no pyridine was added.

The molecular structures of the compounds A and B resulting from the above exemplary methods were investigated by spectroscopic techniques of $^1$H-NMR, $^{13}$C-NMR, FT-IR, mass spectroscopy (MS), and Ultraviolet-visible spectroscopy (UV-Vis).

Figure 3A:
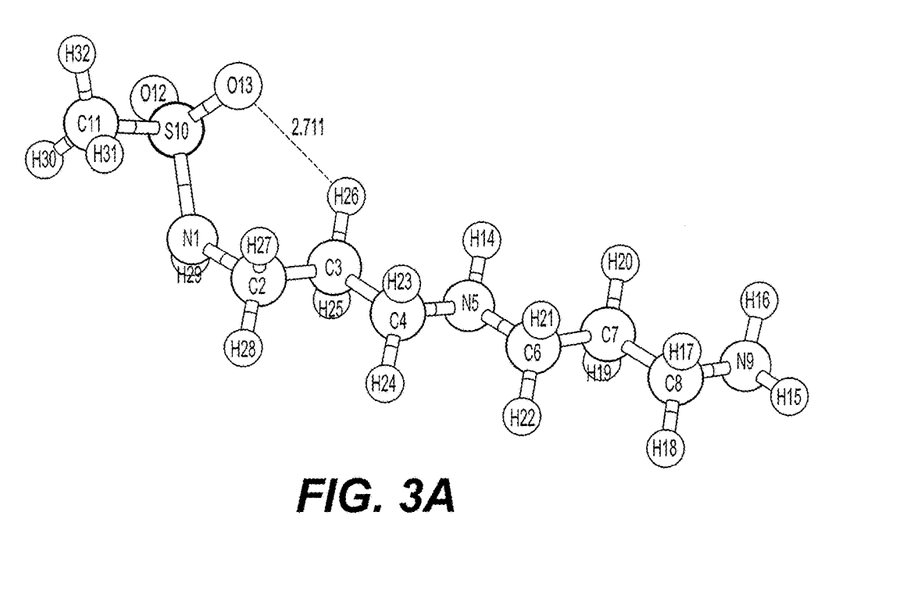
FIGS. 3A and 3B are molecular models showing optimized configurations of compounds A and B, respectively.
Figure 3B:
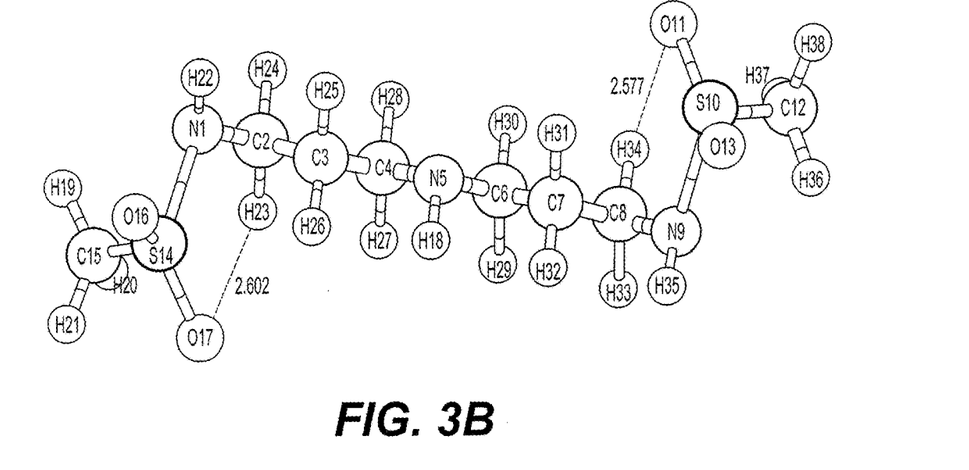
Figure 4:
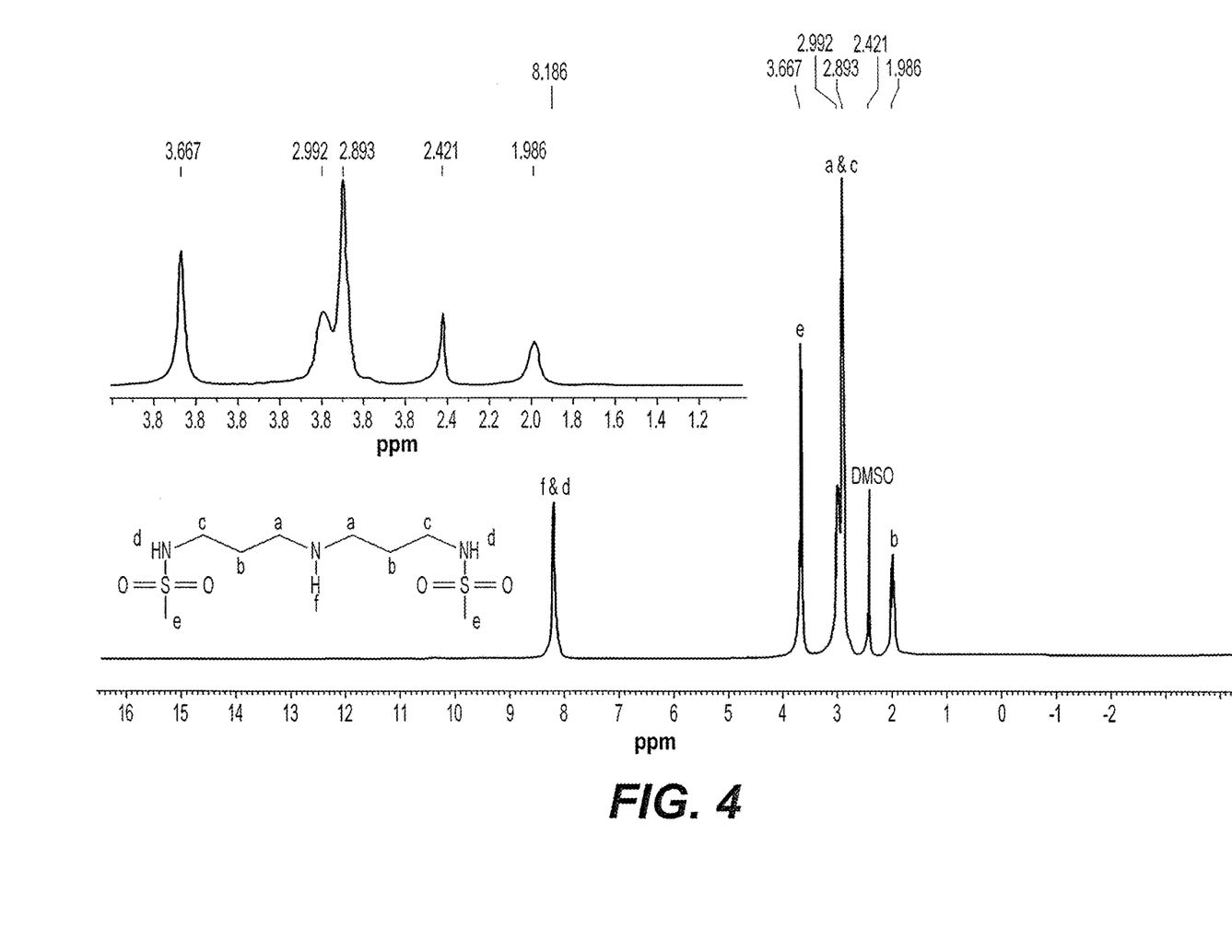
FIG. 4 is the $^1$H nucleic magnetic resonance (NMR) spectrum of compound B.
Figure 5:
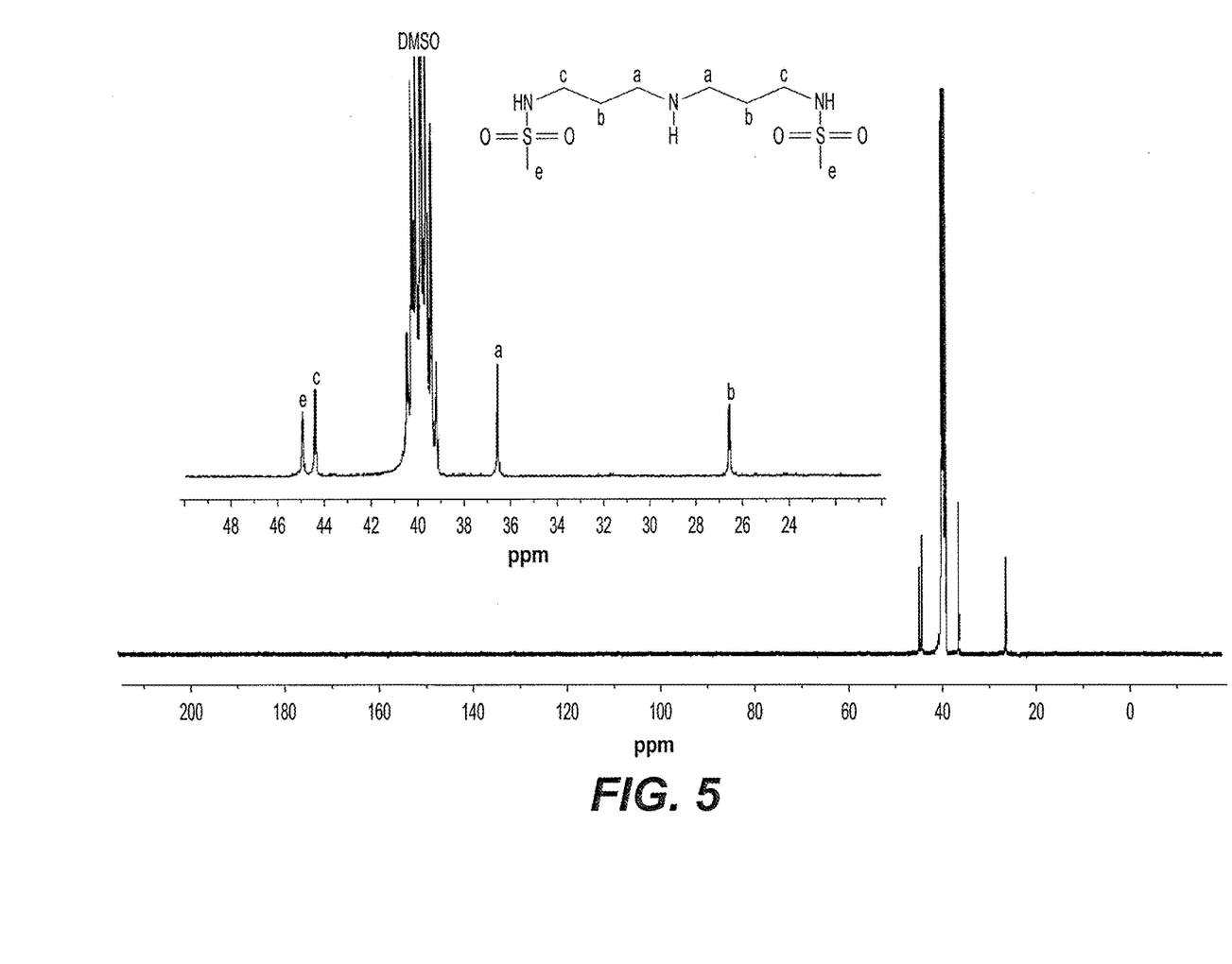
FIG. 5 is the $^{13}$C NMR spectrum of compound B.

FIG. 3 shows optimized structures of compound A (FIG. 3A) and compound B (FIG. 3B) with intra H-bonds, several functional groups with e-rich atoms (such as O, S, and N), in addition to the alkyls groups indicated. FIG. 4 shows the $^1$H-NMR spectrum of compound B in $CDCl_3$. A typical $^1$H-NMR spectrum with high chemical shifts was collected, in which only aliphatic protons were detected from 1-5 ppm (see inset). Chemical shifts are noted directly on the figure. FIG. 5 shows the $^{13}$C-NMR spectrum of compound B in $CDCl_3$. Only aliphatic carbons were detected from 1-50 ppm (see inset). Chemical shifts are noted directly on the figure.

Figure 6:
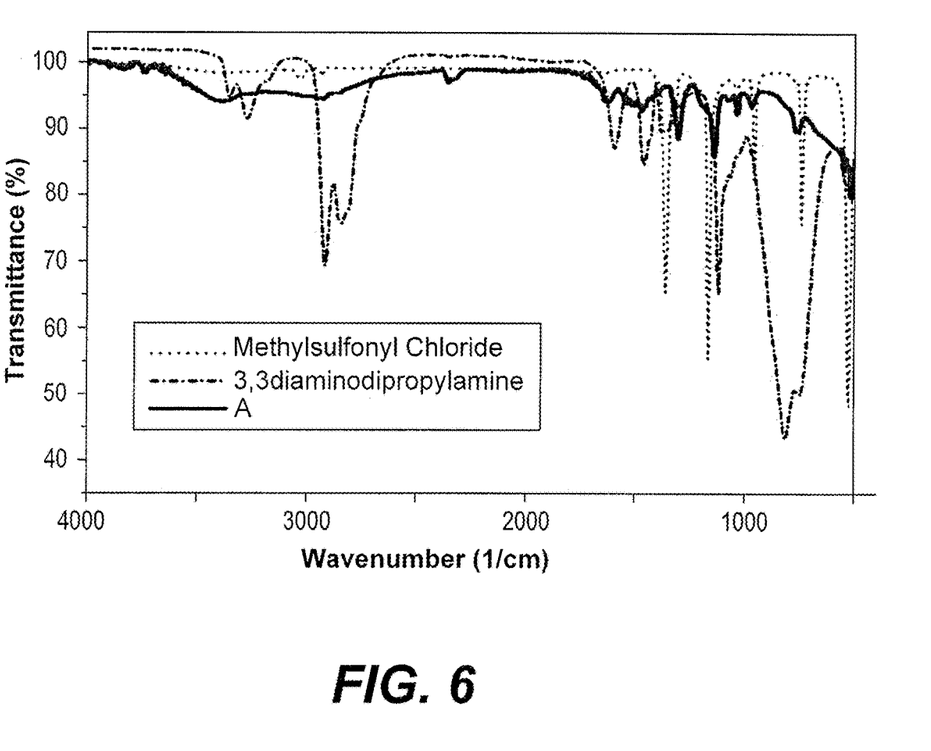
FIG. 6 is the Fourier-transform infrared (FT-IR) spectrum of compound A.

FIG. 6 shows the IR-spectrum of compound A (MP) and starting materials 3,3 diaminodipropylamine and methylsulfonyl chloride, recorded in solid state. The vibrational behavior of each functional group appears with peaks consistent with their expected positions. The main stretching vibration bands of the exemplary compound A spectrum directly correspond to that of the desired compound structural formula. Broad $v_{NH}$ at 3320 $cm^{-1}$, no $v_{(C-H)}$ aromatic vibration, $v_{(C-H)}$ aliphatic at 2980 $cm^{-1}$ and $v_{(S=O)}$ at 1280 $cm^{-1}$.

Figure 7A:
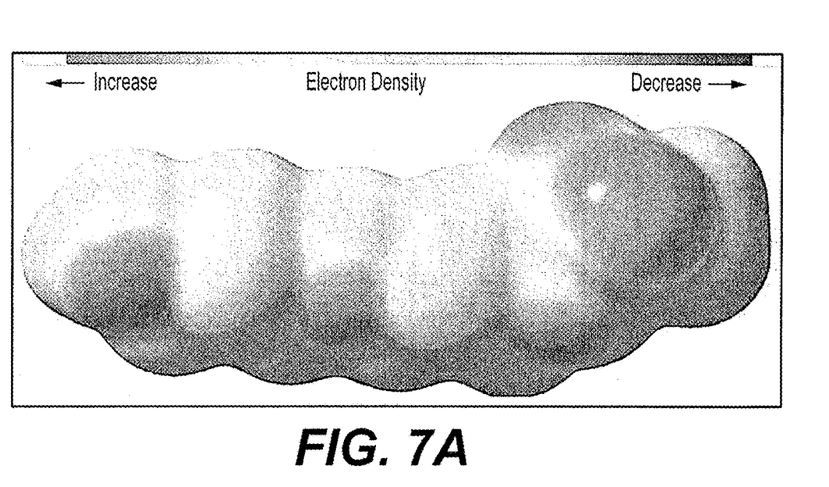
FIGS. 7A and 7B are molecular electrostatic potential (MEP) maps of compound A and compound B, respectively.
Figure 7B:
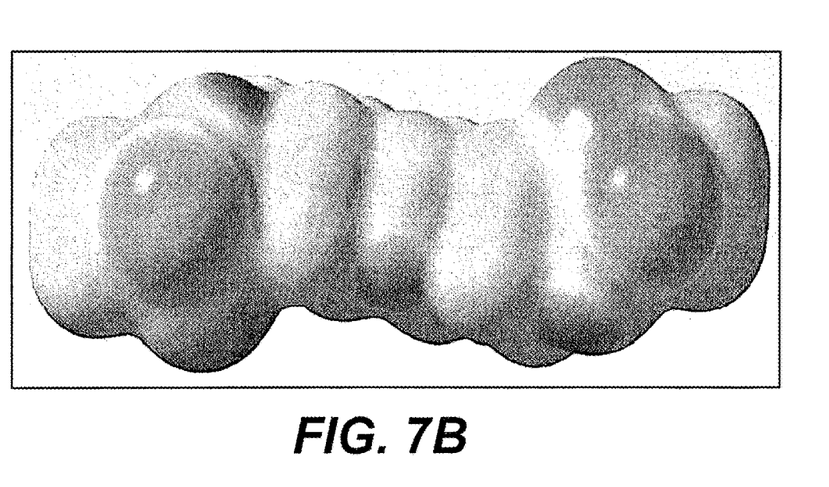
Figure 8:
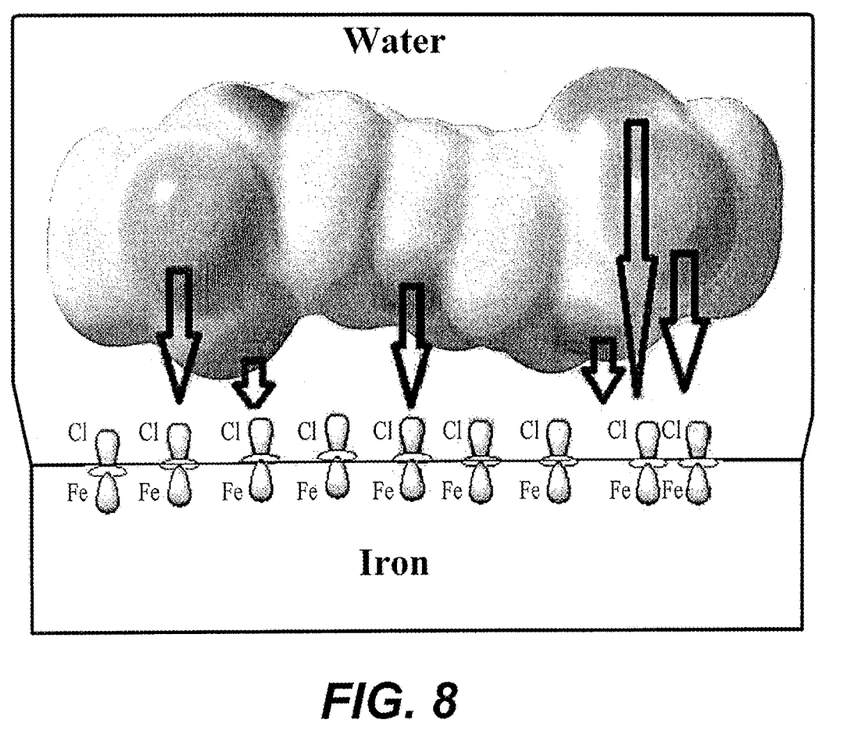
FIG. 8 is a schematic diagram illustrating hypothesized chemisorption behavior of compound B according to and visualized as its MEP map on an iron surface in HCl solution.

Molecular electrostatic potential (MEP) maps of compound A and compound B were prepared, as shown in FIGS. 7A and 7B, respectively, which, as expected, showed increased electron density in locations near the S, N, and O atoms and decreased electron density adjacent the $CH_3$ and $CH_2$ groups. FIG. 8 illustrates the predicted chemisorption behavior of compound B on an iron surface in HCl solution. Lone pairs of 0 atoms attach to the iron positive surface. Meanwhile, the N—H groups attach to the chloride ions on the iron surface.

Example 2

Evaluation of Corrosion Inhibition by Compounds A and B

The activity of exemplary compounds A and B against corrosion of iron alloy in acidic medium was evaluated individually under the following conditions: (1) 0.5M solutions of NaOH, $H_2SO_4$ and HCl at 25° C.; (2) 0.1M, 0.3M, 0.5M solutions of HCl at 25° C., evaluated by both polarization measurements and weight loss measurements; (3) 0.5M solutions of HCl at 25° C., 35° C. and 45° C., evaluated using polarization measurements; and (4) 50 ppm, 100 ppm and 150 ppm of compounds A and B in 0.5 M solution HCl at 25° C.

The electrochemical polarization (EP), electro-impedance spectroscopy (EIS) and weight loss evaluation methods were applied to evaluate the corrosion inhibition activities of compounds A and B. Both compounds A and B exhibit excellent corrosion inhibition activities with an apparent mixed cathodic/anionic mechanism.

Figure 9:
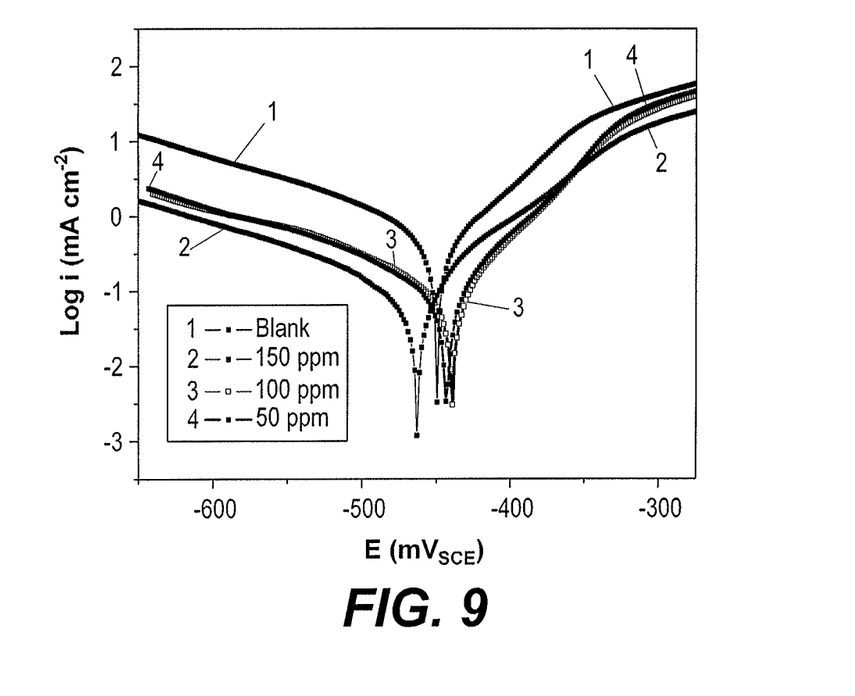
FIG. 9 is a plot of polarization curves for iron in 0.5M HCl with various concentrations of exemplary compound A at 25° C.

FIG. 9 shows polarization curves for iron in 0.5M HCl solution and in the presence of various concentrations of compound B at 25° C. The anodic and cathodic reactions are each affected by the addition of compound B. Indeed, the addition of compound B to HCl solution reduces the anodic dissolution of iron and also retards the cathodic hydrogen evolution reaction, implying that this compound acts as a mixed-type inhibitor with high efficiencies at very low concentrations.

Figure 10:
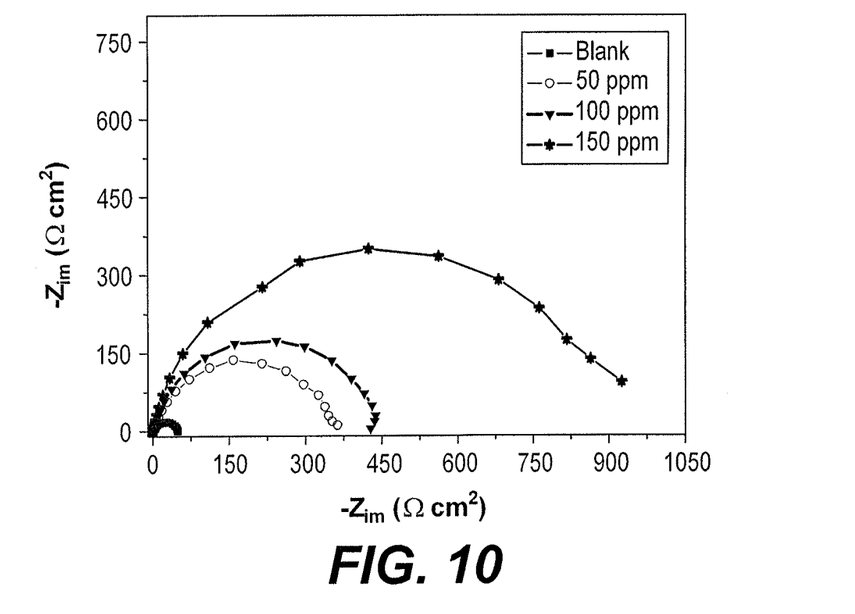
FIG. 10 shows Nyquist plots for iron in 0.5M HCl solution in the absence and presence of various concentrations of exemplary compound B at 25° C.

FIG. 10 shows Nyquist plots for iron in 0.5M HCl solution with 0 ppm, 50 ppm, 100 ppm and 150 ppm of compound B at 25° C. The addition of B to the acidic solution leads to a change of the impedance diagrams in both shape and size. A depressed semicircle at high frequencies and a second time constant appeared at low frequencies. An increase in size of the semicircle with inhibitor concentration indicates increased inhibitor effect. Compound B significantly inhibits corrosion of iron in 1 M HCl, even at very low concentrations.

Figure 11A:
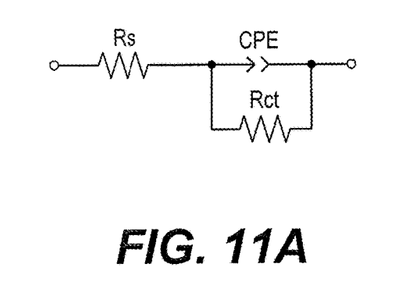
FIG. 11A is a schematic diagram of an electrical equivalent circuit model for the interface between iron and a 0.5M solution of HCl in the absence of a corrosion inhibitor.
Figure 11B:
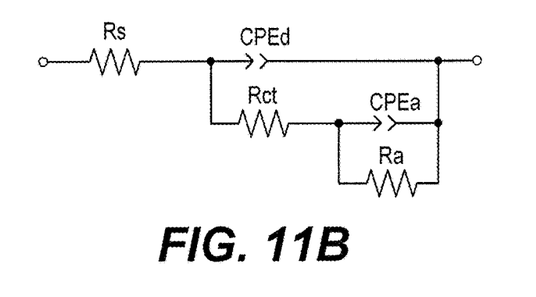
FIG. 11B is a schematic diagram of an electrical equivalent circuit model for the interface between iron and a 0.5M solution of HCl in the presence of the exemplary compound B.
Figure 12:
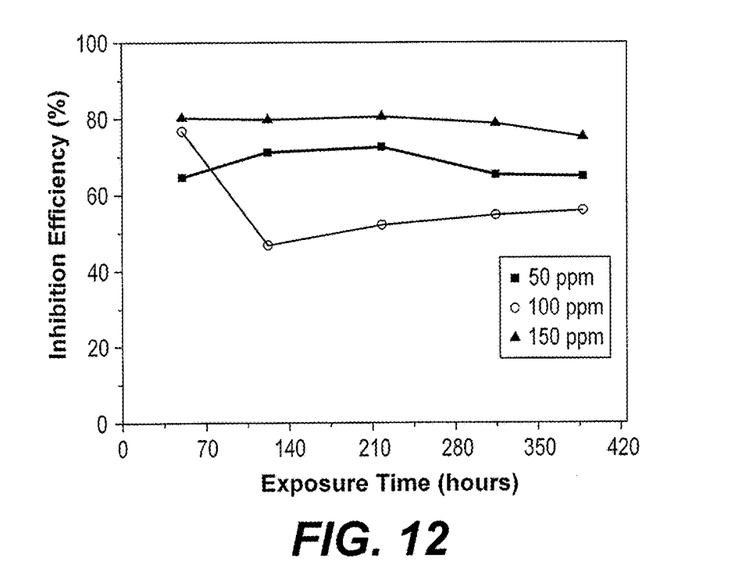
FIG. 12 is a plot of corrosion inhibition efficiency vs. exposure time for iron in 0.5 M HCl solution in the presence of various concentrations of exemplary compound A.

FIGS. 11A and 11B show electrical equivalent circuits for modeling the interface iron in 0.5M HCl solution without (FIG. 11A) and with (FIG. 11B) compound B. Without compound B, a single time constant was observed. In the presence of compound B, a two time constant circuit was proposed to describe the mechanism. In these theoretical circuits, Rs represent the solution resistance, Rct is the charge transfer resistance and CPEd represents the capacitance of the high frequency semicircle that can be attributed to the charge transfer process. Ra represents the resistance of the adsorbed corrosion inhibitor and CPEa is the capacitance of the inhibitor film due to the inhibitor's adsorption on the steel surface.

FIG. 10 shows a plot of inhibition efficiency (%) vs. exposure time of iron in 0.5 M HCl with 0 ppm, 50 ppm, 100 ppm and 150 ppm of compound B at 25° C. From this figure it can be seen that compound B remains effective at a maximum concentration (150 ppm) even at an immersion time of 388 hours, with an efficiency that reached 75%. The results suggest that upon immersion in dilute acidic solution, the sulfonamide corrosion inhibitors form a thin protective film over the workpiece of iron or iron alloy by absorption or chemisorption mechanism modeled in FIG. 8 and continue to protect the workpiece by mixed anodic and cathodic mechanisms.

It is to be understood that the present method is not limited to the embodiments described above, but encompasses any and all embodiments within the scope of the following claims.

We claim:

1. A method for synthesizing an organic corrosion inhibitor, comprising the steps of:
adding a polyamine precursor to a sulfonyl chloride derivative in a solvent, thereby precipitating a by-product and producing the corrosion inhibitor in solution;
removing the precipitated by-product from the solution; and
evaporating the solvent from the solution to isolate the organic corrosion inhibitor in solid form.

2. The method for synthesizing an organic corrosion inhibitor of claim 1, wherein the step of adding the polyamine precursor comprises separately dissolving the polyamine precursor and the sulfonyl chloride derivative, respectively, in anhydrous tetrahydrofuran (THF) and adding the solution of the polyamine precursor to the solution of the sulfonyl chloride derivative dropwise.

3. The method for synthesizing an organic corrosion inhibitor of claim 2, further comprising the step of cooling the solution of the sulfonyl chloride to 0° C. before the step of adding the polyamine precursor.

4. The method for synthesizing an organic corrosion inhibitor of claim 1, further comprising, before removing the precipitated by-product, allowing the solution to react for at least 2 hours under stirring.

5. The method for synthesizing an organic corrosion inhibitor of claim 1, wherein the polyamine precursor is N-(3-aminopropyl)-1,3-propanediamine and the sulfonyl chloride derivative is methanesulfonyl chloride.

6. The method for synthesizing an organic corrosion inhibitor of claim 1, wherein the solvent is tetrahydrofuran.

7. The method for synthesizing an organic corrosion inhibitor according to claim 1, wherein the solvent comprises a mixture of anhydrous tetrahydrofuran and pyridine, the polyamine precursor is 3,3'-diaminodipropylamine, and 1 equivalent of 3-3'-diaminodipropylamine is added to 1 equivalent of the sulfonyl chloride derivative, whereby the synthesized corrosion inhibitor comprises a monosubstituted compound having the formula:

8. The method for synthesizing an organic corrosion inhibitor according to claim 1, wherein the solvent consists of anhydrous tetrahydrofuran, the polyamine precursor is 3,3'-diaminodipropylamine, and 1 equivalent of 3-3'-diaminodipropylamine is added to 2 equivalents of the sulfonyl chloride derivative, whereby the synthesized corrosion inhibitor comprises a disubstituted compound having the formula:

9. A method of inhibiting or preventing corrosion of iron or iron alloys using the corrosion inhibitor prepared by the method of claim 1, comprising the steps of:
  dissolving the corrosion inhibitor in dilute acid solution; and
  bringing the solution of the corrosion inhibitor into contact with the iron or iron alloy to adsorb a thin film of the corrosion inhibitor on a surface of the iron or iron alloy.

10. The method of inhibiting or preventing corrosion according to claim 9, wherein the corrosion inhibitor comprises a compound having the formula:

11. The method of inhibiting or preventing corrosion according to claim 9, wherein the corrosion inhibitor comprises a compound having the formula:

12. A sulfonamide corrosion inhibitor, comprising a compound having the formula:

* * * * *